United States Patent [19]

Clair et al.

[11] 4,010,215

[45] Mar. 1, 1977

[54] PROCESS FOR THE PREPARATION OF TRICHLOROETHYLENE

[75] Inventors: René Clair, Savigny-sur-Orge; Yves Correia, Saint-Auban, both of France

[73] Assignee: Produits Chimiques Pechiney-Saint Gobain, Neuilly-sur-Seine, France

[22] Filed: Feb. 13, 1970

[21] Appl. No.: 11,118

[30] Foreign Application Priority Data

Feb. 21, 1969 France .............................. 69.04472

[52] U.S. Cl. .......................................... 260/654 D
[51] Int. Cl.² ....................................... C07C 21/00
[58] Field of Search ............................... 260/654 D

[56] References Cited

UNITED STATES PATENTS

| | | | |
|---|---|---|---|
| 2,593,451 | 4/1952 | Hill et al. | 260/654 |
| 2,894,045 | 7/1959 | Carley et al. | 260/654 |

*Primary Examiner*—James A. Thomas, Jr.
*Assistant Examiner*—A. Siegel

[57] ABSTRACT

The process of preparing trichloroethylene from 1,1,1,2-tetrachloroethane by decomposition of the tetrachloroethane under a pressure within the range of 1.5 to 10 bars and at a temperature within the range of 135° to 250° C and the treatment of the effluent from the reaction zone for recovery of components thereof.

18 Claims, 1 Drawing Figure

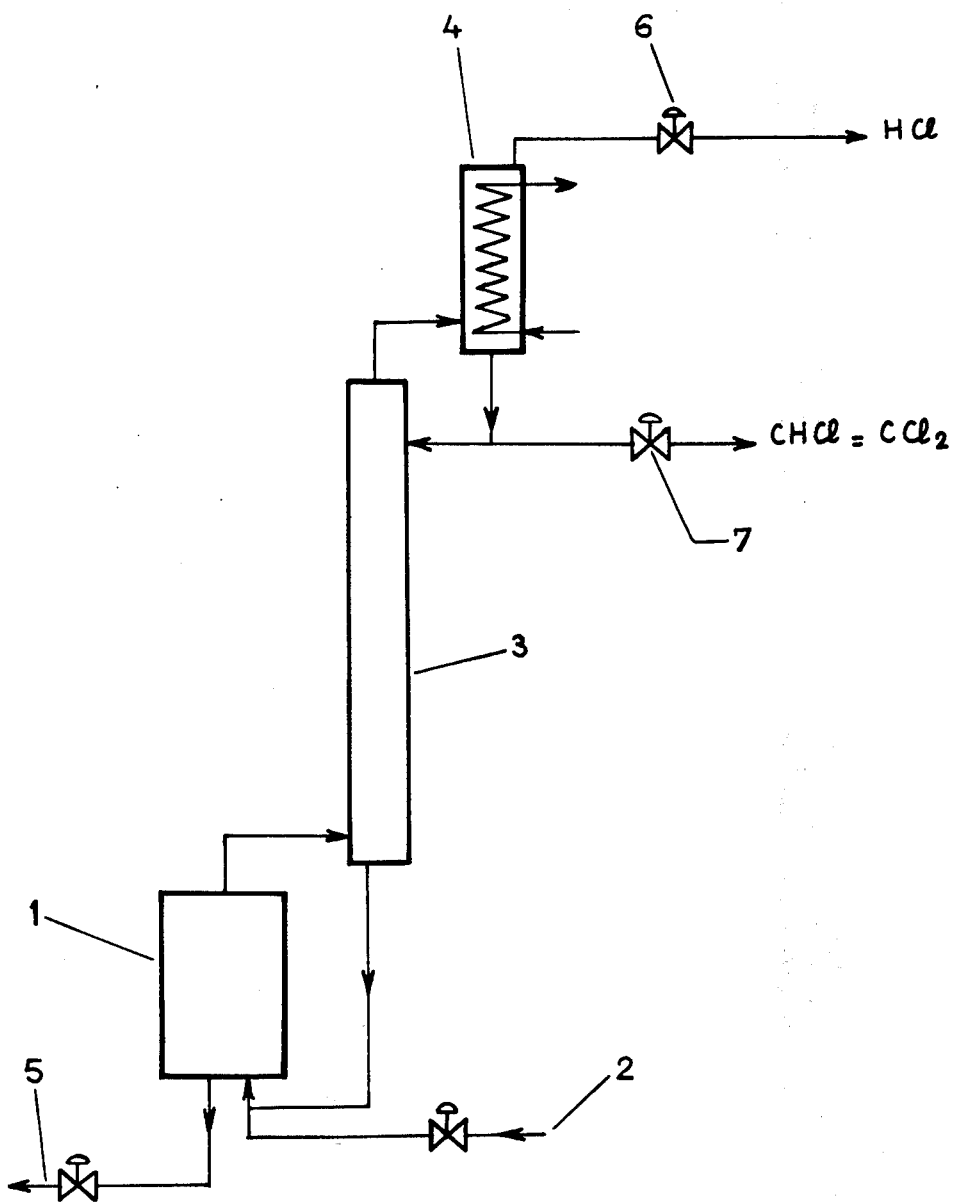

PROCESS FOR THE PREPARATION OF TRICHLOROETHYLENE

This invention relates to the preparation of trichloroethylene by thermal decomposition of 1,1,1,2-tetrachloroethane.

It is known that 1,1,1,2-tetrachloroethane is very slightly unstable to heat and slowly decomposes into hydrochloric acid and trichloroethylene. For instance, when subjected to reflux (at 130° C) in a glass vessel, it has been noticed that the decomposition rate reaches only 0.058 molar percent after 100 hours and that, at a temperature of 158° C under a pressure of 1.45 bar, it does not exceed 0.2 molar percent. This represents a kinetic of decomposition and a yield far too low for industrial exploitation.

It is also known, according to U.S. Pat. No. 2,593,451, that when ferric chloride (from 0.05 to 1% by weight) is put in suspension into 1,1,1,2-tetrachloroethane and that when this suspension is heated to 100°–130° C under atmospheric pressure, good yields in trichloroethylene can be obtained.

Within the framework of this process, the above mentioned U.S. patent says that there is no practical advantage to working under pressures higher than atmospheric pressure. It is also stated that when this reaction is carried out in an iron or steel reactor, the ferric chloride can be obtained in situ by introducing into the reactor the corresponding quantity of chlorine which reacts with the iron or steel surface of the reactor to yield ferric chloride as the active catalyst. Introduction of molecular chlorine into the reaction medium may give rise to side reactions with the chlorinated compounds present, more particularly the unsaturated chlorinated compounds, such as trichloroethylene present in the said reaction medium. These side reactions produce saturated chlorinated hydrocarbons. Furthermore, in a continuous process, the trichloroethylene obtained contains $FeCl_3$ in suspension which must be eliminated by means of decantation and/or filtration operations, since during distillation in the presence of $FeCl_3$, trichloroethylene tends to polymerize and give tars. Moreover, in this reaction the use of a catalyst becomes critical for it is very sensitive to impurities such as moisture, which impurities tend to cause the ferric chloride to lose its catalytic activity. This results in irregular operation of the process or the need for supplementary treatment of the initial products in order to eliminate these impurities.

It is an object of this invention to remove these drawbacks while enabling thermal decomposition of 1,1,1,2-tetrachloroethane at a pressure above atmospheric pressure and in the absence of a ferric chloride suspension, thus eliminating the problem of the catalyst separation and of its deactivation, with the decomposition rate of 1,1,1,2-tetrachloroethane reaching 90 molar percent and even about 97 molar percent.

It has been found in an unexpected way that, contrary to the teaching in the U.S. Pat. No. 2,593,451, the application of a pressure above atmospheric pressure enables improved yields in trichloroethylene in the absence of a ferric chloride suspension in unsymmetrical tetrachloroethane.

According to the process of this invention, there is introduced continuously, in the liquid state, 1,1,1,2-tetrachloroethane or a mixture of chlorinated hydrocarbons containing at least 15 molar percent and preferably more than 30 molar percent of 1,1,1,2-tetrachloroethane, into a metallic enclosure forming the walls of a reaction zone where decomposition of 1,1,1,2-tetrachloroethane is achieved under a pressure ranging from 1.5 to 10 bars, at a temperature ranging from 135° to 250° C in order to maintain in the boiling state the liquid phase containing the 1,1,1,2-tetrachloroethane introduced into the said reaction zone.

In the event that the 1,1,1,2-tetrachloroethane subjected to the decomposition reaction is in admixture with other compounds $C_1 - C_2$ chlorinated and $C_4$ chlorinated compounds (heavy products) such as carbon tetrachloride, chloroform, ethyl chloride, dichloroethanes, 1,1,2-trichloroethane 1,1,2,2-tetrachloroethane, pentachloroethane, trichloroethylene, perchloroethylene, hexachlorobutenes, hexachlorobutadiene and tarry chlorinated products $> C_4$, the said reaction is achieved selectively and these other chlorinated compounds are practically unmodified except for a small part (less than 30 and most often less than 20 molar %) of the pentachloroethane which may be present, which yields perchloroethylene and hydrochloric acid in a corresponding amount. As a result, these chlorinated compounds may be considered as practically inert diluents since they practically do not influence the decomposition reaction of the 1,1,1,2-tetrachloroethane. In the event that 1,1,1-trichloroethane is present in the admixture with the 1,1,1,2-tetrachloroethane subjected to dehydrochlorination, it also undergoes dehydrochlorination simultaneously with 1,1,1,2-tetrachloroethane but yields 1,1-dichloroethylene and hydrochloric acid.

According to this invention, the residence time of 1,1,1,2-tetrachloroethane or of the mixture containing same in the reaction zone depends on the adpoted operating conditions, but generally it is within the range of 15 minutes and 4 hours, and preferably is between 90 and 150 minutes, with the shortest residence times being employed for the highest temperature and pressure conditions, and the longest residence times for the lowest temperature and pressure conditions. In a continuous process, the residence time in hours is defined in this specification as being the ratio of the quantity expressed in moles of the liquid phase in the reaction zone to the feed flow rate expressed in moles per hour of 1,1,1,2-tetrachloroethane or of the mixture containing it. However, residence times above 4 hours, such as for instance up to 10 hours, may be used to operate the dehydrochlorination of 1,1,1,2-tetrachloroethane into trichloroethylene with conversion rates near 100%, but, as far as an industrial exploitation is concerned, it is preferable to limit the conversion rate to a value within the range of 50 and 90 molar percent consistent with a maximum hourly production of trichloroethylene under working conditions which are the easiest to apply. For instance, when working under a pressure of 10 bars, the conversion rate is in the range of 95 molar percent for a residence time of 20 minutes. However, the equipment must be specially adapted to sustain such a pressure. On the other hand, it is easier to operate with less elaborated equipment under a pressure of 6 or 7 bars, although the residence time is longer, ranging from 1 to 1.75 hours in order to obtain the same conversion rate as when operating under 10 bars.

According to a particular embodiment of this process, the metallic walls of the enclosure for the reaction zone are of iron or iron-alloys, containing at least 1% by weight of Fe, such as alloys known under the names of monel and inconel and preferably with more than 90% by weight of Fe, such as ordinary steel or pig iron.

The preferred temperature and pressure conditions are in the range from 170° to 200° C and from 3 to 6 bars respectively.

It has been found that in order to obtain stable operating conditions within the framework of a continuous process, it is preferable to feed the reaction zone regularly with 1,1,1,2-tetrachloroethane or with a mixture containing it, and to maintain a constant level of liquid in the reaction zone.

According to one embodiment of the continuous process, in the steady operating state, two effluents are formed which exit from the reaction zone: on the one hand, a gaseous effluent containing mainly hydrochloric acid and trichloroethylene, accompanied with 1,1,1,2-tetrachloroethane vapors or with the mixture containing 1,1,1,2-tetrachloroethane, each one of the components being present in an amount proportional to its concentration in the liquid phase and to its vapor pressure at the pressure and at the temperature of said reaction zone, and, on the other hand, a liquid effluent containing trichloroethylene dissolved in 1,1,1,2-tetrachloroethane which has not reacted or in the mixture containing it, as well as a very small proportion of dissolved hydrochloric acid (0.05% by weight).

In order to achieve the separation of the various components of the gaseous effluent, the latter can be treated in a distillation zone under a pressure corresponding to the working pressure in said reaction zone and which is generally within the range of 1.5 and 10 bars.

It is thus convenient to surmount the reaction zone by a distillation zone composed of a concentration column, and to achieve distillation under the same pressure, taking into consideration pressure losses prevailing in said reaction zone.

The concentration column is equipped overhead with a condensation zone essentially of trichloroethylene. The chlorinated derivatives, having a higher boiling point, flow back to the bottom of the concentration column and return to the reaction zone. The hydrochloric acid is collected in the form of a gaseous effluent from said condensation zone.

The liquid effluent of the reaction zone, which contains traces of dissolved iron (<0.0025% by weight) can be subjected to distillation in order to recover any trichloroethylene dissolved therein, and to eliminate the very small proportion of hydrochloric acid.

The distillation residue, which contains 1,1,1,2-tetrachloroethane, alone or in admixture with other chlorinated and particularly $C_2$ hydrocarbons, such as 1,1,2,2-tetrachloroethane, pentachloroethane and perchloroethylene, may be recycled to the reaction zone.

According to a preferred form of treatment of the liquid effluent of the reaction zone, it is used directly as feed of a heat treatment furnace, without filling of solid material, in order to complete the decomposition of unsymmetrical tetrachloroethane in the vapor phase by heat and possibly of symmetrical tetrachloroethane, 1,1,1-trichloroethane and of pentachloroethane which may be present according to a method wherein the wall temperature of said furnace is from 450° to 550° C under a pressure of 1 to 7 bars with a residence time of the reagents ranging from 0.2 to 12 seconds.

Trichloroethylene and possibly perchloroethylene, which may be present in the feed mixture of said treatment furnace, are not affected by this treatment.

According to a variation of the continuous process of the invention it is operated in the steady state in order to form only a single effluent which is gaseous and which exits from said reaction zone and which is composed of vapors of hydrochloric acid, trichloroethylene and 1,1,1,2-tetrachloroethane or of a mixture containing 1,1,1,2-tetrachloroethane. Each of the components of this mixture is present in an amount proportional to its concentration in the liquid phase and to its vapor pressure at the pressure and the temperature at which the decomposition is achieved in said reaction zone. This gaseous effluent can be used directly, without any previous separation, that is to say, without distillation nor condensation zones, as feed of a heat treatment furnace, having no filling of solid material, in order to complete the decomposition in the vapor phase by heating 1,1,1,2-tetrachloroethane and possibly 1,1,2,2-tetrachloroethane, 1,1,1-trichloroethane and pentachloroethane which may be present according to a method in which the wall temperature of said furnace ranges from 450° to 550° C and wherein the reagents are subjected to a pressure of 1 to 7 bars with a residence time ranging from 0.2 to 12 seconds. Under these conditions there can be allowed a slight purge (<2% by weight of the feed) through a point of said reaction zone with the aim of eliminating the tarry heavy residues.

This invention has also for an object, an apparatus for the practice of the process, an embodiment of which is illustrated schematically by the appended FIGURE.

This apparatus comprises a metallic reactor 1, of the thermosyphon evaporator type, equipped with a nest of tubes (not represented in the FIGURE). A feeding system 2 enabling the introduction of 1,1,1,2-tetrachloroethane or of the mixture containing it into said reactor. This reactor is surmounted with a packed concentration column 3 and a condenser 4 which achieve directly the separation of the hydrochloric acid and of the trichloroethylene formed. The liquid reflux, at the bottom of the column 3, is recycled to the reactor 1. A bleeding off at 5 is achieved preferably on this reactor in order to maintain a constant volume of reaction liquid in the reactor 1.

A system comprising a regulation device of the working pressure (not represented in the FIGURE), located overhead of the condenser 4, drives a valve 6. The working pressure of between 1.5 and 10 bars is obtained owing to the development of hydrochloric acid, the flow rate of which, issuing from the apparatus, is checked by the above-mentioned pressure regulation system. A heating system, as by heat transfer fluid (not represented in the FIGURE) enables practically constant temperature to be maintained on the external wall of the above-mentioned nest of tubes of said reactor and to obtain, in this manner, a regular pressure loss in column 3. Finally a valve 7 is regulated in order to obtain trichloroethylene of at least a purity of 99%.

The following examples are given by way of illustration and not by way of limitation of the various aspects of this invention and must not be considered as limitative.

EXAMPLE 1

Into the ordinary steel reactor 1 of the appended FIGURE, there are introduced continuously 10 moles per hour of 1,1,1,2-tetrachloroethane of 99.8% purity, the main impurity being composed of a mixture of hexachlorobutenes. The temperature of the liquid reaction medium in the reactor is 170° C and the prevailing pressure is of 5 bars. The residence time of the liquid in the reactor is about 2.5 hours. Under these conditions, 9 moles per hour of hydrochloric acid are collected at the top of the condenser and 9 moles/hour of trichloroethylene of 99.5% purity through valve 7.

There is achieved only a slight bleeding-off of the liquid phase of the reactor, of the order of 1 molar percent with respect to the feed so as to avoid the building up of the concentration of impurities present in this feed. The liquid reaction medium in the reactor is composed of 40 molar percent of 1,1,1,2-tetrachloroethane and of 60 molar percent of trichloroethylene. The decomposition rate of 1,1,1,2-tetrachloroethane is thence 90%. The liquid phase of the reactor includes 10 mg/kg of dissolved iron. The very small volume bled off is treated by distillation in order to remove these impurities (chlorinated heavy products > $C_2$) and the distillate is recycled to the reactor 1.

EXAMPLE 2

Into the reactor of Example 1, 14 moles/hour of a mixture composed of 50 molar percent of 1,1,1,2-tetrachloroethane and of 50 molar percent of 1,1,2,2-tetrachloroethane are introduced continuously. The temperature of the liquid reaction medium is 190° C and the pressure is 5 bars. The residence time of the liquid in the reactor is about 2 hours. There are thus collected 6.51 moles/hour of hydrochloric acid at the heat of condenser 4 of Example 1 and 4.81 moles/hour of trichloroethylene of 99.3% purity through valve 7. The effluent of the reactor comprises 9.19 moles/hour of a mixture composed of:

| | |
|---|---|
| trichloroethylene | 1.70 mole |
| unsymmetrical tetrachloroethane | 0.49 mole |
| symmetrical tetrachloroethane | 7.0 mole |

The decomposition rate of the unsymmetrical tetrachloroethane is 93%. The liquid effluent of reactor 1 is free of tars and heavy products and contains 15 mg/kg of dissolved $FeCl_3$. This effluent serves as feed for the evaporator of a thermal cracking furnace (not represented in the appended FIGURE) operating at 500° C under a pressure of 5 bars and wherein the effluent is in the vapor phase. The residence time of the reagents in this furnace is about 1.5 seconds. At the exit of the furnace, 95 molar percent of the tetrachloroethanes are converted into trichloroethylene and hydrochloric acid. After separation of the hydrochloric acid, the mixture is introduced continuously into a column fed with a 80 g/l milk of lime and steam, the last traces of tetrachloroethanes are converted into trichloroethylene which distils in the form of a heteroazeotrope.

As a comparative test, the working conditions of Example 2 are repeated except that the pressure is 1 bar thus corresponding to a temperature of 142° C in the reactor, all other operating conditions being identical to those of Example 2. Under these conditions, there is obtained a slight evolution of hydrochloric acid which varies in course of time, but which remains between 0.5 and 10 molar percent of the 1,1,1,2-tetrachloroethane involved, while in Example 2 the decomposition rate of 1,1,1,2-tetrachloroethane, under a pressure of 5 bars, is 93%.

EXAMPLE 3

Into the reactor forming part of the apparatus of Example 1, there are introduced continuously 15 moles/hour of a mixture containing:
   9.3 moles of 1,1,1,2-tetrachloroethane
   4.5 moles of 1,1,2,2-tetrachloroethane
   1.2 moles of pentachloroethane The reactor temperature is raised to 190° C and the pressure is regulated at 5.5 bars. The residence time of the liquid in the reactor is about 2 hours. Under these conditions, there are collected 8.83 moles/hour of hydrochloric acid at the head of the condenser, 8.22 moles/hour of trichloroethylene of the distillate and 6.78 moles/hour of liquid effluent of the reactor which contains:
   0.61 mole of trichloroethylene
   0.47 mole of 1,1,1,2-tetrachloroethane
   4.5 moles of 1,1,2,2-tetrachloroethane
   1.2 moles of pentachloroethane Under these conditions, the decomposition rate of the 1,1,1,2-tetrachloroethane is 95%.

The liquid effluent of the reactor is free of tars and of heavy products and contains 12 mg/kg of dissolved $FeCl_3$. This effluent is used in order to feed an evaporator with thermosyphon being in direct connection with a thermal cracking furnace which is without a filling, and which operates at 470° C, under a pressure of 3.5 bars and where this effluent is in the vapor phase. The reaction time of the reagents in this furnace and its accessory parts is 8 seconds. At the exit of the accessory parts of the furnace 93% of the tetrachloroethanes are converted into trichloroethylene and hydrochloric acid and 80% of the pentachloroethane into perchloroethylene and hydrochloric acid. The vapors leaving the accessory parts of the furnace are condensed by cooling, thus letting hydrochloric acid escape in the gaseous state. After neutralization by means of lime, the condensate is rectified in order to obtain pure trichloroethylene.

EXAMPLE 4

Into the reactor which is part of the apparatus of Example 1, there are introduced continuously 11 moles/hour of a mixture composed of:
   3.77 moles of 1,1,1,2-tetrachloroethane
   5.60 moles of 1,1,2,2-tetrachloroethane
   1.43 moles of pentachloroethane
   0.20 mole of heavy products (chlorinated $C_4$ hydrocarbons)

The temperature of the liquid reaction medium is 200° C and the pressure is regulated at 5.5 bars. The residence time of the liquid in the reactor is about 2 hours. Under these conditions, there are collected: 3.70 moles/hour of hydrochloric acid at the head of condenser 4; 3.47 moles of this acid originate from the decomposition of 1,1,1,2-tetrachloroethane and 0.23 mole from the decomposition of pentachloroethane.

The distillate is composed of 3.07 moles/hour of trichloroethylene. Moreover, a liquid effluent of the reactor is collected representing 7.93 moles/hour of a mixture composed of:
   0.40 mole of trichloroethylene
   0.23 mole of perchloroethylene
   0.30 mole of 1,1,1,2-tetrachloroethane
   5.60 moles of 1,1,2,2-tetrachloroethane
   1.20 moles of pentachloroethane 0.20 mole of chlorinated heavy products (>$C_4$ hydrocarbons)

The decomposition rate of 1,1,1,2-tetrachloroethane is 92% and that of pentachloroethane is 16%.

The liquid effluent of the reactor is free of tars and contains about 20 mg/kg of dissolved $FeCl_3$. This effluent serves as feed for the evaporator of a thermal cracking furnace operating at 500° C under a pressure of 5 bars and where the effluent is in the vapor phase. The residence time of the reagents in the furnace is 2 seconds. At the exit of the furnace, 92.5 molar percent of the tetrachloroethanes are converted into trichloroethylene and hydrochloric acid and 75 molar percent of the pentachloroethane are converted into perchloroethylene and hydrochloric acid. After separation of the hydrochloric acid, the mixture is introduced continuously into a column fed with a 80 g/l milk of lime and steam, the last traces of tetrachloroethanes are converted into trichloroethylene which is distilled in the form of a heteroazeotrope. After decantation and drying, the rectification enables obtaining pure trichloroethylene. The distillate residue contains perchloroethylene and pentachloroethane which were at the exit of said thermal cracking furnace. They are separated by distillation.

EXAMPLE 5

Into the reactor which is part of the apparatus of Example 1, there are introduced continuously 100 moles/hour of a mixture composed of:

37 moles/hour of 1,1,1,2-tetrachloroethane
50 moles/hour of 1,1,2,2-tetrachloroethane
13 moles/hour of pentachloroethane and containing traces of heavy chlorinated products with a number of carbon atoms above 2.

The pressure in the reactor is 4.5 bars and the residence time of the liquid in the reactor is about 20 minutes. The temperature of the vapors which escape from the reactor is in the range from 210° to 215° C and this vapor phase has the following molar composition:

20.7 of hydrochloric acid
20.6 of trichloroethylene
8.7 of 1,1,1,2-tetrachloroethane
39.7 of 1,1,2,2-tetrachloroethane
10.3 of pentachloroethane No bleeding off of the liquid phase is achieved, except the discontinuous purge of about 2 molar percent of the initial mixture in order to avoid the accumulation of heavy chlorinated products, thus giving a conversion rate of 1,1,1,2-tetrachloroethane close to 70%, that of pentachloroethane being practically nil. This vapor effluent is sent into a thermal cracking furnace operating at 500° under a pressure of 4.5 bars. The contact time of the reagents at this temperature is 4 seconds. At the exit of the furnace, 94 molar percent of the tetrachloroethanes are converted into trichloroethylene and 60% of the pentachloroethane is converted into perchloroethylene. The trichloroethylene which was in the feed of the furnace is not affected by this treatment.

After separation of the hydrochloric acid, the mixture of chlorinated hydrocarbons is neutralized and rectified in order to separate trichloroethylene, perchloroethylene and pentachloroethane.

EXAMPLE 6

Into the reactor which is part of the apparatus of Example 1, there are introduced continuously 10 moles/hour of a mixture containing:

8 moles of 1,1,1,2-tetrachloroethane
1.5 moles of 1,1,2,2-tetrachloroethane
0.5 mole of pentachloroethane.

The reactor temperature is 190° C and the pressure about 5 bars. The residence time of the liquid in the reactor is about 2 hours. Under these conditions there are collected 7.65 moles/hour of hydrochloric acid at the head of the condenser, 7.1 moles of trichloroethylene and 2.9 moles/hour of liquid effluent which contains:

0.5 mole of trichloroethylene
0.4 mole of 1,1,1,2-tetrachloroethane
1.5 mole of 1,1,2,2-tetrachloroethane about 0.5 mole of pentachloroethane containing traces of perchloroethylene.

The conversion rate of the 1,1,1,2-tetrachloroethane is close to 95%.

The liquid effluent which contains about 12 mg/kg of dissolved $FeCl_3$ feeds a column which, in addition to this effluent, receives a 100 g/l. milk of lime and steam which enables converting quantitatively 1,1,2,2-tetrachloroethane and pentachloroethane into trichloroethylene and perchloroethylene, a portion only of the 1,1,1,2-tetrachloroethane being dehydrochlorinated into trichloroethylene. The chlorinated products are collected at the head of the column in the form of a heteroazeotrope. After decantaion and drying, the rectification enables obtaining pure trichloroethylene.

We claim:

1. A process of preparing trichloroethylene from 1,1,1,2-tetrachloroethane comprising continuously introducing 1,1,1,2-tetrachloroethane in the liquid state into a metallic walled reaction zone, decomposing said 1,1,1,2-tetrachloroethane under a pressure within the range of 3 to 6 bars and at a temperature within the range of 135° to 250° C to maintain in ebullition the liquid phase containing 1,1,1,2-tetrachloroethane introduced into said reaction zone.

2. A process as claimed in claim 1 in which the 1,1,1,2-tetrachloroethane is in admixture with other chlorinated hydrocarbons, which mixture contains at least 15 molar percent of 1,1,1,2-tetrachloroethane.

3. A process as claimed in claim 2 in which said mixture of chlorinated hydrocarbons, in addition to 1,1,1,2-tetrachloroethane, contains chlorinated $C_1$, $C_2$ and >$C_2$ compounds.

4. A process as claimed in claim 1 in which the residence time in the reaction zone is within the range of 15 minutes and 4 hours.

5. A process as claimed in claim 1 in which the temperature and the pressure are within the range of 170° to 200° C and 3 to 6 bars respectively.

6. A process as claimed in claim 1 in which the reaction zone is fed with a regular flow of 1,1,1,2-tetrachloroethane or of a mixture containing same by maintaining a constant liquid level in the reaction zone.

7. A process as claimed in claim 1 in which two effluents are issued from the reaction zone, namely: a gaseous effluent containing mainly hydrochloric acid and trichloroethylene, accompanied by vapors of 1,1,1,2-tetrachloroethane or of the mixture containing 1,1,1,2-tetrachloroethane in which each of the components of this mixture is present in an amount proportional to its concentration in the liquid phase and to its vapor pressure under the pressure and temperature conditions existing in the reaction zone, and a liquid effluent containing trichloroethylene dissolved in the 1,1,1,2-tetrachloroethane which has not reacted or the 1,1,1,2-tetrachloroethane which is present in the mixture and which has not reacted as well as a very small proportion of hydrochloric acid.

8. A process as claimed in claim 7 in which the hydrochloric acid in the liquid effluent is less than 0.05%.

9. A process as claimed in claim 7 in which the gaseous effluent is treated in a distillation zone composed of a concentration column under a pressure within the range of 3 to 6 bars, distillation being achieved under substantially the same pressure within pressure losses as that prevailing in said reaction zone.

10. A process as claimed in claim 9 in which a condensation zone is located at the head of the distillation zone wherein trichloroethylene essentially and hydrochloric acid is captured as gaseous effluent in said condensation zone.

11. A process as claimed in claim 7 in which the liquid effluent of the reaction zone is subjected to distillation to recover the trichloroethylene which is dissolved therein and to eliminate the very slight proportion of hydrochloric acid and the distillation residue which contains 1,1,1,2-tetrachloroethane which has not reacted is recycled to said reaction zone.

12. A process as claimed in claim 7 in which the liquid effluent of the reaction zone is fed to a thermal treatment furnace, without filling of solid material in order to complete the vapor phase decomposition of 1,1,1,2-tetrachloroethane and possibly of 1,1,2,2-tetrachloroethane, 1,1,1-trichloroethane and pentachloroethane which may be present, at a temperature within the range of 450° to 550° C under a pressure ranging from 1 to 7 bars and with a contact time of reagents ranging from 0.2 to 12 seconds.

13. A process as claimed in claim 1 in which only a single gaseous effluent is evolved from said reaction zone and is composed of hydrochloric acid vapors, trichloroethylene and 1,1,1,2-tetrachloroethane or of a mixture containing 1,1,1,2-tetrachloroethane, each one of the components of this mixture being present in an amount proportional to its concentration in the liquid phase and to its vapor pressure under the pressure and temperature conditions existing in the reaction zone.

14. A process as claimed in claim 13 in which the gaseous effluent is fed directly to a thermal treatment furnace, without filling of solid material, to complete vapor phase decomposition by heat of 1,1,1,2-tetrachloroethane and possibly of 1,1,2,2-tetrachloroethane, 1,1,1-trichloroethane and of the pentachloroethane which may be present, at a temperature ranging from 450° to 550° C, under a pressure ranging from 1 to 7 bars and with a contact time of reagents ranging from 0.2 to 12 seconds.

15. A process as claimed in claim 14 which includes purging the reaction zone with less than 2% by weight of the feed.

16. A process as claimed in claim 1 in which the metallic walled reaction zone is made of iron.

17. A process as claimed in claim 1 in which the metallic enclosure for the reaction zone is made of iron alloys containing at least 1% by weight of iron.

18. A process as claimed in claim 1 in which the metallic enclosure for the reaction zone is made of iron alloys containing more than 90% by weight of iron.

* * * * *